United States Patent [19]

Bieringer et al.

[11] 4,336,057
[45] Jun. 22, 1982

[54] HERBICIDES

[75] Inventors: Hermann Bieringer, Eppstein; Reinhard Handte, Hofheim am Taunus, both of Fed. Rep. of Germany

[73] Assignee: Hoechst Aktiengesellschaft, Frankfurt am Main, Fed. Rep. of Germany

[21] Appl. No.: 192,309

[22] Filed: Sep. 30, 1980

Related U.S. Application Data

[63] Continuation of Ser. No. 26,876, Apr. 4, 1979, abandoned.

[30] Foreign Application Priority Data

Apr. 8, 1978 [DE] Fed. Rep. of Germany ....... 2815287

[51] Int. Cl.$^3$ ..................... A01N 43/00; A01N 43/02
[52] U.S. Cl. ........................................... 71/88; 71/90; 71/91; 71/93; 71/111
[58] Field of Search ................................ 71/88, 90, 91

[56] References Cited

U.S. PATENT DOCUMENTS

| 3,708,277 | 1/1973 | Zeidler et al. | 71/91 |
| 3,868,245 | 2/1975 | Fischer | 71/91 |
| 4,130,413 | 12/1978 | Handte et al. | 71/90 |
| 4,165,977 | 8/1979 | Fischer | 71/91 |

Primary Examiner—Glennon H. Hollrah
Attorney, Agent, or Firm—Curtis, Morris & Safford

[57] ABSTRACT

Herbicides containing in combination
(A) compounds of the formula I

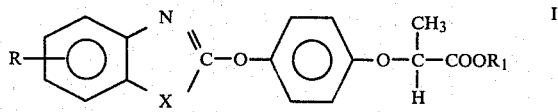

in which
R is chlorine or bromine,
X is oxygen or sulfur, and
$R_1$ is hydrogen, ($C_1$–$C_4$)-alkyl or a cation equivalent; and (B) compounds of the formulae $B_1$:

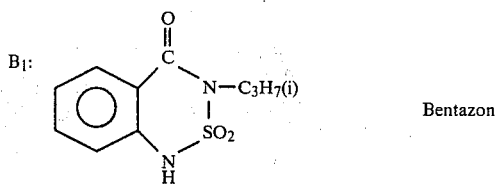

Bentazon or $B_2$:

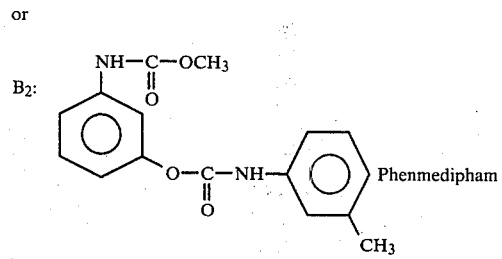

Phenmedipham or $B_3$:

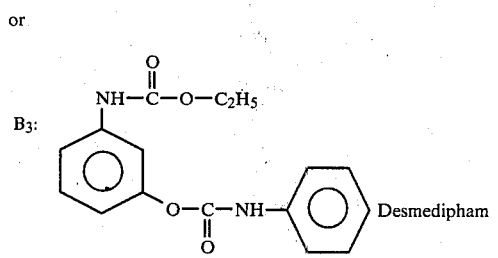

Desmedipham or $B_4$:

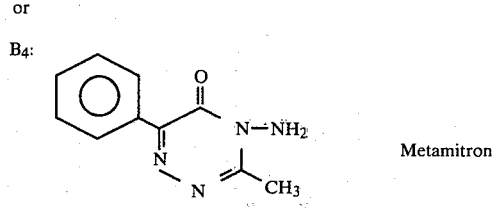

Metamitron as active components, the weight ratio of components A to B being preferably from 5:1 to 1:20. These herbicidal combinations are distinguished by a synergistic effect, especially against weed grasses in crop plants.

3 Claims, No Drawings

HERBICIDES

This is a continuation, of application Ser. No. 26,876 filed Apr. 4, 1979, now abandoned.

It is known that many herbicides, although having a good activity against dicotyledonous weeds, are insufficiently or even not at all effective against weed grasses. Examples of these compounds are Bentazon [3-isopropyl(1H)-2,1,3-benzothiadiazin-4(3H)-one-2,2-dioxide], Phenmedipham [3-methoxycarbonylaminophenyl-(3-methylphenyl)carbamate], Desmedipham [3ethoxycarbonylaminophenyl-phenylcarbamate] and Metamitron (4-amino-3-methyl-6-phenyl1,2,4,-triazin-5(4H)-one.

Furthermore, compounds have been disclosed recently which have a good selectivity with respect to economically important weed grasses such as wild oat (Avena), annual blackgrass (Alopecurus spp.) annual meadow grass (Poa spp.), ray grass (Lolium spp.), annual and perennial wild millets (Echinochloa spp , Setaria spp., Digitaria spp., Panicum spp., Sorghum spp.), Bermuda grass (Cynodon spp.) and quack grass (Agropyron spp.) Examples of compounds having a special activity against such weed grasses are the heterocyclically substituted 4-oxyphenoxy-propionic acid derivatives described in German Offenlegungsschrift No. 2,640,730.

It has now been found that combinations of the cited compounds surprisingly display a synergistic effect in combating weed grasses. Such properties are considered as being novel inventions having economic importance (Colby S.R. 1967; Calculating Synergistic and Antagonistic Responses of Herbicide Combinations—Weeds 15, 20–22).

The subject of the present invention concerns herbicides containing an effective amount of a combination of (A) compounds of the formula I

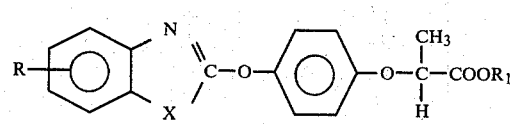

in which
R is chlorine or bromine,
X is oxygen or sulfur, and
$R_1$ is hydrogen, $(C_1-C_4)$-alkyl or a cation equivalent; and (B) compounds of the formulae

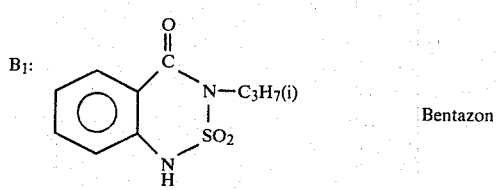

Bentazon or

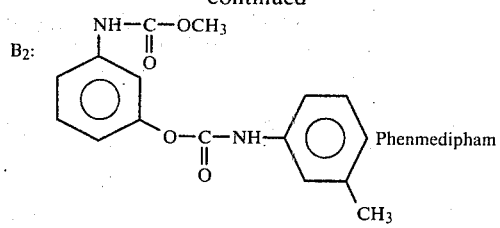

Phenmedipham or

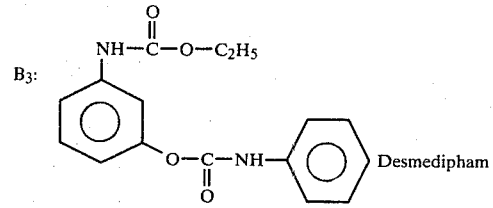

Desmedipham or

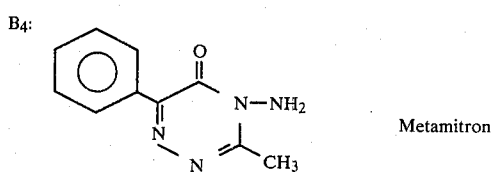

Metamitron

Instead of the racemic compounds of the formula I, the optical antipodes, especially the D-(+) form, may alternatively be used in the combinations of the invention.

The mixing ratio A:B may vary within wide limits of from about 5:1 to 1:20. The correct ratio depends on the prevailing weed spectrum, the development stage of the weeds, and the mixing component. Preferably, a mixing ratio of from 3:1 to 1:6 is chosen.

The herbicidal combinations in accordance with this invention can be applied either in the form of tank mixtures, where the active ingredients are mixed immediately before their application, or in the form of ready-for-use formulations. In this latter case, they are formulated as wettable powders, emulsifiable concentrates, sprayable solutions, dusting agents, or granules, and may contain the usual formulation auxiliaries such as wetting agents, adhesives, dispersing agents, solid or liquid inert substances and grinding auxiliaries or solvents.

Wettable powders are formulations which are uniformly dispersible in water and which, in addition to the active compound and a diluent or inert material, also contain wetting agents, for example, polyoxethylated alkylphenols, polyoxethylated oleylamines or stearylamines, alkylsulfonates or alkylphenylsulfonates and dispersing agents, for example sodium ligninsulfonate, sodium, 2,2'-dinaphthylmethane-6,6'-disulfonate, or the sodium salt of oleoyl-methyl-taurine.

Emulsifiable concentrates are obtained by dissolving the active compound in an organic solvent, for example, butanol, cyclohexanone, dimethylformamide, xylene or even higher-boiling aromatics, and adding a non-ionic wetting agent, for example, a polyoxyethylated alkylphenol or a polyoxyethylated oleylamine or stearylamine.

Dusting agents are obtained by grinding the active compound with finely divided solids, for example talc, natural clays, such as kaolin, bentonite, pyrophilite or diatomaceous earth.

Granules can be manufacture either by spraying the active compound onto absorbent, granular inert material or by applying active compound concentrates by means of adhesives, for example polyvinyl alcohol, sodium polyacrylate or even mineral oils, onto the surfaces of carriers, such as sand, kaolinites or granular inert material. Suitable formulations can also be manufactured by the customary methods of manufacture of fertilizer granules, if desired in admixture with fertilizers.

In the herbicidal products the concentrations of the active compounds in the commercial formulations may vary. In wettable powders, the active compound concentration varies, for example, between about 10 to 95%, the remainder consisting of one or more of the abovementioned formulation additives. In the case of emulsifiable concentrates, the active compound concentration is about 10% to 80%. Dust formulations usually contain 5–20% of active compound, and sprayable solutions about 2–20%. In the case of granules, the active compound content in part depends on whether the active compound is in a liquid or solid form and what granulating auxiliaries, fillers and the like are used.

If necessary or desired the commercial concentrates may be diluted prior to application in the usual manner, for example by means of water in the case of wettable powders and emulsifiable concentrates. Dusts, granules and sprayable solutions are generally ready for use without further dilution. The amount of active ingredient necessary for obtaining the desired results depends on external conditions such as temperature, humidity and the like. It may vary within wide limits, (0.1 and 10.0 kg/ha).

The active compounds according to the invention can be combined with other herbicides, insecticides, and fungicides; further herbicidal substances can be added for combating special weeds.

The following Examples illustrate the invention.

FORMULATION EXAMPLES

Example A

An emulsifiable concentrate is obtained from
15 parts by weight of active substance (A+B)
75 parts by weight of cyclohexanone as solvent, and
10 parts by weight of oxethylated nonyl phenyl (10 EO) as emulsifier.

Example B*

A wettable powder which is easily dispersible in water is obtained by mixing
25 parts by weight of active substance A+B
64 parts by weight of quartz containing kaolin as inert material
10 parts by weight of potassium lignosulfonate and
1 part by weight of sodium oleoyl-methyl-taurine as wetting and dispersing agent and grinding the mixture in a pin mill.

Example C*

A dusting powder is obtained by mixing
10 parts by weight of active substance A+B and
90 parts by weight of talc as inert material and comminuting the mixture in a hammer mill.

Example D*

A granular formulation consists, for example, of about
2 to 15 parts by weight of active substance A+B and
98 to 85 parts by weight of inert granular materials such as attapulgite, pumice and quartz sand.

(*) In the Examples B, C and D, the individual active substances were formulated separately and subsequently ground in common.

BIOLOGICAL EXAMPLES

Example I

In a greenhouse, the herbicides indicated in Table I, alone or as mixtures, were applied in the post-emergence process to plants previously grown and being 18 days old. The tests were repeated 4 times. 4 weeks after the treatment, the test results were visually evaluated and the percental damage of the crop plants and weeds determined. Thus, it is shown that the effect against grasses of components A in the mixture is synergistically increased, that the sugar beet is not damaged and the activity against Chenopodium is not deteriorated.

Example II

Under similar conditions as indicated in Example I, the compounds listed in Table II were applied in the post-emergence process to corresponding crop plants and weeds (plants being 18 days old). The test results demonstrate that the growth of the crop plant (soybean) is not adversely affected, and the activity against wild oat is synergistically increased in the combination of A+B, while the activity against dicotyledonous weeds of component B in admixture with A is not substantially altered.

Example III

Under greenhouse conditions, the products listed in Table III were applied in the post-emergence process to plants in pots being 4 weeks old. Also in this case, the tests were repeated 4 times. After a further 4 weeks, the herbicidal effect was determined visually. The percental damage values listed in Table III prove again the synergistic effect against annular blackgrass and demonstrate that the individual components as well as herbicidal mixtures are tolerated by sugar beets.

The results of these three greenhouse tests prove that there is in all cases a special increase of herbicidal activity against weed grasses, which is of synergistic nature. For example, the synergistic effect is such that in the case of combination A+B half the amount of components A has the same activity against weed grasses as has component A when used alone, although component B per se has a very insufficient activity or none at all against weed grasses. On the other hand, the effect of components B against broad-leaf weeds is not substantially increased. The crop plant is not damaged or adversely affected by the mixtures.

In all three Examples, novel, economically important, synergistic effects have been found which cause a substantial increase of activity of the weed grass herbicide components (and thus a reduction of the application amounts required).

TABLE I

Herbicidal activity and acceptability in the post-emergence process (damage in %)

| Component | Dosage kg AS/ha | Sugar beet | Wild oat Avena fatua | Chenopodium album |
|---|---|---|---|---|
| A₁ | 0.12 | 0 | 8 | 0 |
|  | 0.25 | 0 | 49 | 0 |
|  | 0.5 | 0 | 97 | 40 |
| B₂ | 0.5 | 0 | 40 | 57 |
|  | 1.0 | 0 | 40 | 96 |
| A₁ + B₂ | 0.12 + 0.5 | 1 | 96 | 95 |
| B₄ | 0.5 | 0 | 51 | 100 |
| A₁ + B₄ | 0.12 + 0.5 | 0 | 91 | 100 |

A₁: ethyl-2-[4-(6-chloro-2-benzothiazolyloxy)-phenoxy]-propionate
AS = active substance

TABLE II

Herbicidal action and acceptability in post-emergence (damage in %)

| Component | Dosage kg AS/ha | soybean | Wild oat Avena fatua | Solanum nigrum | Chenopodium album |
|---|---|---|---|---|---|
| A₁ | 0.12 | 0 | 8 | 0 | 0 |
|  | 0.25 | 0 | 49 | 0 | 0 |
|  | 0.5 | 0 | 97 | 0 | 40 |
| B₁ | 0.5 | 0 | 0 | 83 | 75 |
|  | 1.0 | 0 | 24 | 95 | 95 |
| A₁ + B₁ | 0.12 + 0.5 | 1 | 70 | 86 | 78 |
|  | 0.25 + 0.5 | 2 | 100 | 89 | 79 |

TABLE III

Activity and acceptability in crop plants (damage in %)

| Component | Dosage kg AS/ha | Sugar beet | Annual blackgrass Alopecurus myos. |
|---|---|---|---|
| A₂ | 0.3 | 0 | 0 |
|  | 0.06 | 0 | 28 |
|  | 0.12 | 0 | 49 |
|  | 0.25 | 0 | 87 |
| B₄ | 0.5 | 0 | 14 |
| A₂ + B₄ | 0.03 + 0.5 | 0 | 49 |
|  | 0.06 + 0.5 | 0 | 65 |
|  | 0.12 + 0.5 | 0 | 73 |
| B₃ | 0.25 | 0 | 0 |
|  | 0.50 | 0 | 0 |
| A₂ + B₃ | 0.03 + 0.25 | 0 | 49 |
|  | 0.06 + 0.25 | 0 | 59 |

A₂: ethyl-2-[4-(6-chloro-2-benzoxazolyloxy)-phenoxy]-propionate

What is claimed is:

1. A herbicidal composition consisting essentially of an effective amount of a combination of
(A) a compound of the formula

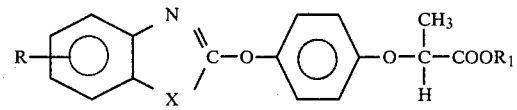

in which R is chlorine or bromine, X is oxygen or sulfur, and R₁ is hydrogen, sodium, potassium, ammonium or alkyl of 1 to 4 carbon atoms; and
(B) the compound of the formula

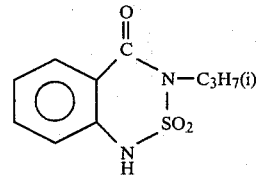

wherein the proportion by weight of components A and B is in the range of 1:2 to 1.2:5.

2. A herbicidal composition as defined in claim 1 in which component A is 2-[4-(6-chloro-2-benzoxazolyloxy)phenoxy]-propionic acid, 2-[4-(5-chloro-2-benzoxazolyloxy)phenoxy]-propionic acid, 2-[4-(6-chloro-2-benzothiazolyloxy)phenoxy]-propionic acid, or sodium, potassium or ammonium salt thereof, or a 1 to 4 carbon alkyl ester thereof.

3. A method of combating weed grasses in crop plants which comprises applying thereto a herbicidally effective amount of the herbicidal composition defined in claim 1.